US00PP26614P2

(12) United States Plant Patent
Wood

(10) Patent No.: US PP26,614 P2
(45) Date of Patent: Apr. 19, 2016

(54) ***VITEX* PLANT NAMED 'SMVACBD'**

(50) Latin Name: *Vitex Agnus-castus*
Varietal Denomination: SMVACBD

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 105 days.

(21) Appl. No.: 14/120,740

(22) Filed: Jun. 21, 2014

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — C. A. Whealy

(57) ABSTRACT

A new and distinct cultivar of *Vitex* plant named 'SMVACBD', characterized by its compact and upright plant habit; moderately vigorous growth habit; freely branching habit; full and dense plants; freely flowering habit; violet blue-colored flowers that are held above and beyond the foliar plane on upright panicles; and good garden performance.

2 Drawing Sheets

Botanical designation: *Vitex Agnus-castus.*
Cultivar denomination: 'SMVACBD'.

BACKGROUND OF THE INVENTION

The present invention relates to a new and distinct cultivar of *Vitex* plant, botanically known as *Vitex Agnus-castus* and hereinafter referred to by the name 'SMVACBD'.

The new *Vitex* plant is a product of a planned breeding program conducted by the Inventor in Grand Haven, Mich. The objective of the breeding program is to create new compact and uniform *Vitex* plants with attractive leaf and flower coloration.

The new *Vitex* plant originated from an open-pollination in July, 2008 in Grand Haven, Mich. of an unnamed selection of *Vitex Agnus-castus*, not patented, as the female, or seed, parent with an unknown selection of *Vitex Agnus-castus* as the male, or pollen, parent. The new *Vitex* plant was discovered and selected by the Inventor as a single flowering plant within the progeny of the stated cross-pollination in a controlled environment in Grand Haven, Mich. in July, 2011.

Asexual reproduction of the new *Vitex* plant by softwood cuttings in a controlled environment in Grand Haven, Mich. since July, 2011 has shown that the unique features of this new *Vitex* plant are stable and reproduced true to type in successive generations.

SUMMARY OF THE INVENTION

Plants of the new *Vitex* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMVACBD'. These characteristics in combination distinguish 'SMVACBD' as a new and distinct *Vitex* plant:

1. Compact and upright plant habit.
2. Moderately vigorous growth habit.

3. Freely branching habit; full and dense plants.
4. Freely flowering habit.
5. Violet blue-colored flowers that are held above and beyond the foliar plane on upright panicles.
6. Good garden performance.

Plants of the new *Vitex* can be compared to plants of the female parent selection. Plants of the new *Vitex* differ primarily from plants of the female parent selection in plant size as plants of the new *Vitex* are compact and about half the size of the female parent selection. In addition, plants of the new *Vitex* have smaller inflorescences than plants of the female parent selection.

Plants of the new *Vitex* can be compared to plants of *Vitex Agnus-castus* 'Shoal Creek', not patented. In side-by-side comparisons conducted in Grand Haven, Mich., plants of the new *Vitex* differed from plants of 'Shoal Creek' in the following characteristics:

1. Plants of the new *Vitex* were much more compact than plants of 'Shoal Creek'.
2. Plants of the new *Vitex* had smaller inflorescences than plants of 'Shoal Creek'.
3. Flowers of plants of the new *Vitex* were darker in color than flowers of plants of 'Shoal Creek'.

BRIEF DESCRIPTION OF THE PHOTOGRAPHS

The accompanying colored photographs illustrate the overall appearance of the new *Vitex* plant showing the colors as true as it is reasonably possible to obtain in colored reproductions of this type. Colors in the photographs may differ slightly from the color values cited in the detailed botanical description which accurately describe the colors of the new *Vitex* plant.

The photograph on the first sheet comprises a side perspective view of a typical flowering plant of 'SMVACBD' grown in an outdoor nursery.

The photograph on the second sheet is a close-up view of a typical flowering plant of 'SMVACBD'.

DETAILED BOTANICAL DESCRIPTION

The aforementioned photographs and following observations and measurements describe plants grown during the summer in an outdoor nursery in Grand Haven, Mich. and under cultural practices typical of commercial *Vitex* production. Plants were two years old when the photographs were taken and three years old when the description was taken. In the following description, color references are made to The Royal Horticultural Society Colour Chart, 1995 Edition, except where general terms of ordinary dictionary significance are used.

Botanical classification: *Vitex Agnus-castus* 'SMVACBD'.

Parentage:

*Female, or seed, parent.*—Unnamed selection of *Vitex Agnus-castus*, not patented.

*Male, or pollen, parent.*—Unknown selection of *Vitex Agnus-castus*, not patented.

Propagation:

*Type.*—By softwood cuttings.

*Time to initiate roots, summer.*—About 20 days at temperatures about 22° C.

*Time to produce a rooted young plant, summer.*—About three months at temperatures about 22° C.

*Root description.*—Fine, fibrous.

*Rooting habit.*—Freely branching; dense.

Plant description:

*Plant form and habit.*—Perennial deciduous shrub; compact and upright plant habit; inverted triangle; freely branching habit with about 68 lateral branches developing per plant; full and dense plant habit; moderately vigorous growth habit.

*Plant height.*—About 1 meter.

*Plant diameter.*—About 1.5 meters.

Lateral branch description:

*Length.*—About 63 cm.

*Diameter.*—About 5 mm.

*Internode length.*—About 5 cm.

*Strength.*—Strong.

*Aspect.*—Upright to about 45° from vertical.

*Fragrance.*—Aromatic when broken.

*Texture, developing.*—Slightly pubescent.

*Texture, developed.*—Smooth, glabrous.

*Color, developing.*—Close to 166A.

*Color, developed.*—Close to 199A.

Leaf description:

*Arrangement.*—Opposite, palmately compound with five to seven leaflets per leaf.

*Leaflet.*—About 10 cm.

*Leaflet width.*—About 2.5 cm.

*Leaflet shape.*—Oblanceolate.

*Apex.*—Acute.

*Base.*—Cuneate to slightly obtuse.

*Margin.*—Entire.

*Texture, upper surface.*—Smooth, glabrous.

*Texture, lower surface.*—Slightly pubescent.

*Venation pattern.*—Pinnate.

*Color.*—Developing leaves, upper surface: Close to 147A. Developing leaves, lower surface: Close to 191A. Fully expanded leaves, upper surface: Close to 147A; midvein, close to 143A; lateral venation, close to 147B. Fully expanded leaves, lower surface: Close to 147B and 191A; venation, close to 143C.

*Petioles.*—Length: About 2 mm. Diameter: About 1.5 mm. Texture, upper and lower surfaces: Smooth, glabrous. Color, upper and lower surfaces: Close to 147A.

Inflorescence & flower description:

*Flower arrangement and habit.*—Single campanulate flowers arranged in terminal panicles; flowers face mostly upward, outward or downward; freely flowering habit with about 212 flowers developing per inflorescence.

*Natural flowering season.*—Plants flower continuously during the late summer, late August to mid-September in Michigan.

*Flower longevity on the plant.*—Flowers last about four to eight weeks; flowers persistent.

*Fragrance.*—Aromatic.

*Inflorescence length.*—About 16 cm.

*Inflorescence diameter.*—About 3 cm.

*Flowers.*—Appearance: Five-lobed campanulate. Diameter: About 8 mm. Depth (height): About 1 cm.

*Flower buds.*—Length: About 6 mm. Diameter: About 2 mm. Shape: Elliptical to obovate. Color: Close to 191A to 191B.

*Corolla.*—Arrangement: Single whorl of five fused petals; one larger than the other four. Petal length, largest petal: About 4 mm. Petal length, smaller four petals: About 3 mm. Petal width, largest petal: About 3.5 mm. Petal width, smaller four petals: About 2 mm. Petal lobe shape, all petals: Oblong. Petal lobe apex, all petals: Obtuse. Petal lobe margin, all petals: Entire. Petal texture, all petals, upper and lower surfaces: Smooth, glabrous. Color, all petals: When opening and fully opened, upper surface: Close to 89A. When opening and fully opened, lower surface: Close to 92C.

*Calyx.*—Arrangement: Single whorl of five fused sepals; calyx campanulate in shape. Length: About 1 mm. Diameter: About 1 mm. Sepal apex: Acute. Sepal margin: Entire. Sepal texture, upper and lower surfaces: Smooth, glabrous. Sepal color, upper and lower surfaces: Close to 191B.

*Peduncles.*—Length: About 16 cm. Diameter: About 2 mm. Strength: Strong. Aspect: Mostly erect. Texture: Smooth, glabrous. Color: Close to 174A and 138B.

*Pedicels.*—Length: About 3 mm. Diameter: About 1 mm. Strength: Strong, flexible. Aspect: About 30° to 90° from peduncle axis. Color: Close to 197C.

*Reproductive organs.*—Stamens: Quantity: Four per flower. Anther size: About 1 mm by 2 mm. Anther shape: Oblong. Anther color: Close to 202B. Pollen amount: Moderate. Pollen color: Close to 202B. Pistils: Quantity: One per flower. Pistil length: About 3 mm. Stigma shape: Globular. Stigma color: Close to 138C. Style length: About 2.8 mm. Style color: Close to 92A. Ovary color: Close to 138C. Seeds and fruits: Seed and fruit development have not been observed on plants of the new *Vitex*.

Garden performance: Plants of the new *Vitex* have been observed have good garden performance as exhibited by its tolerance to rain, wind and drought. Plants of the new *Vitex* have been observed to tolerate temperatures ranging from about −27° C. to about 41° C.

Pathogen & pest resistance: Plants of the new *Vitex* have not been observed to be resistant to pathogens and pests common to *Vitex* plants.

It is claimed:

1. A new and distinct *Vitex* plant named 'SMVACBD' as illustrated and described.

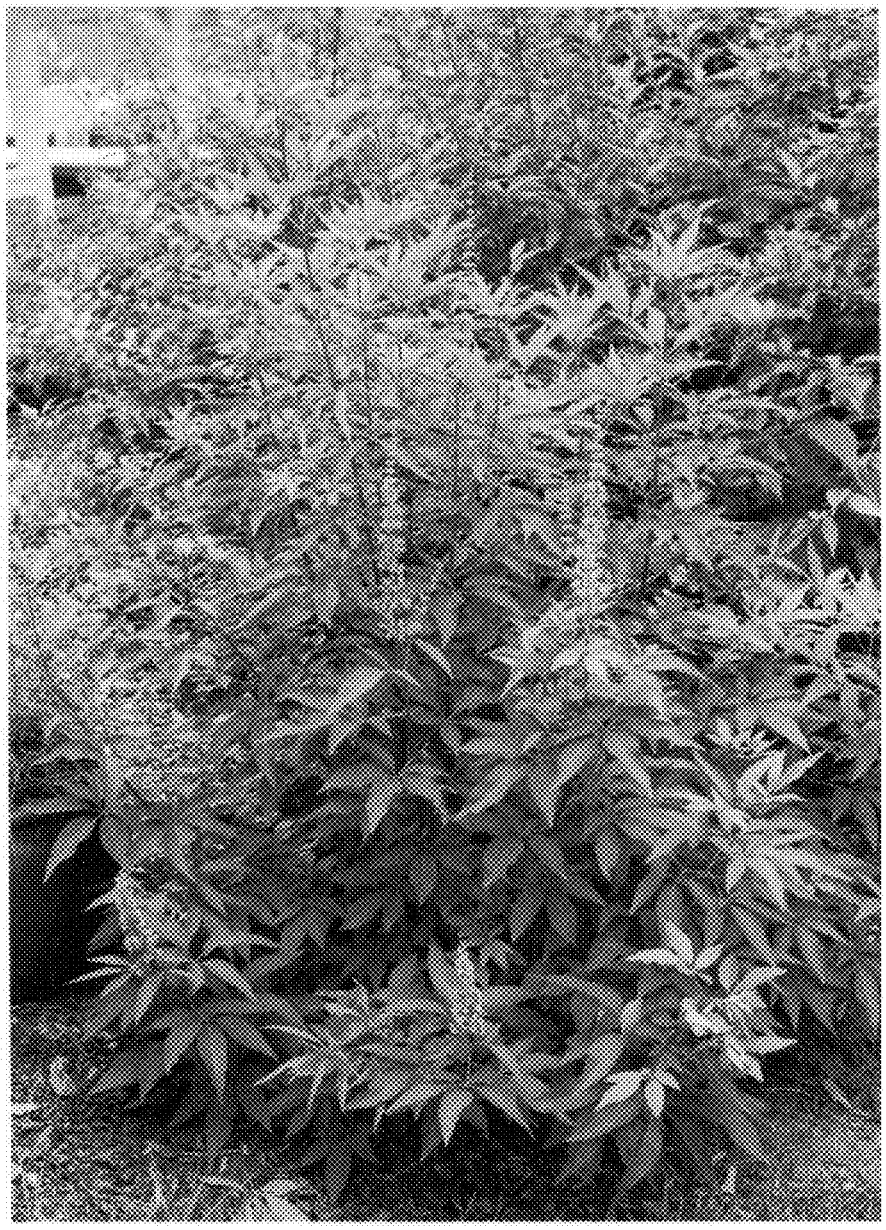

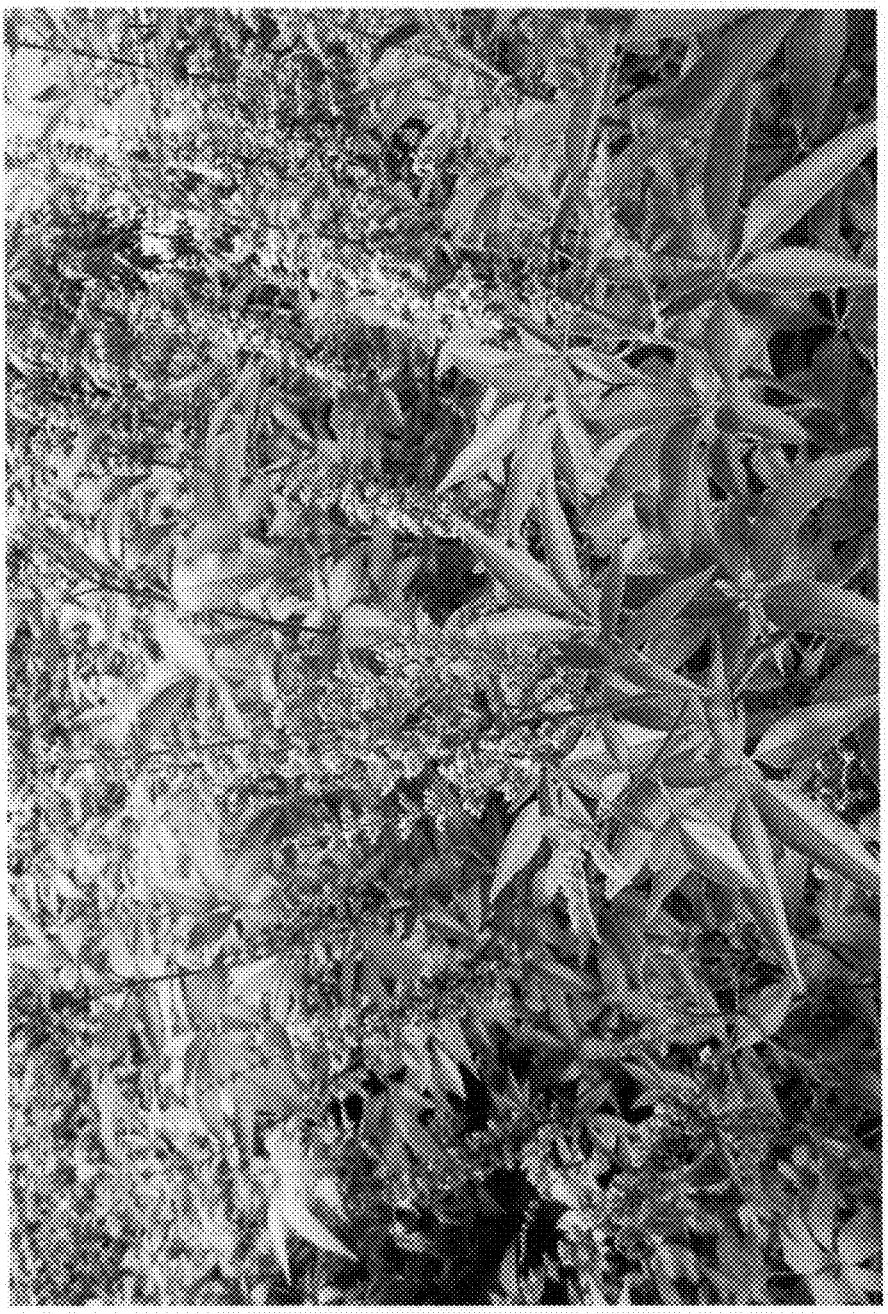

* * * * *